United States Patent
Evans et al.

(10) Patent No.: US 6,709,811 B1
(45) Date of Patent: Mar. 23, 2004

(54) VERSATILE REAGENT FOR DETECTING MURINE LEUKEMIA VIRUSES

(75) Inventors: Leonard H Evans, Hamilton, MT (US); William J Britt, Birmingham, AL (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 1,826 days.

(21) Appl. No.: 08/046,352

(22) Filed: Apr. 8, 1993

Related U.S. Application Data

(63) Continuation of application No. 07/528,714, filed on May 24, 1990, now abandoned.

(51) Int. Cl.[7] .............................. C12Q 1/70; C12N 5/20; C07K 16/10
(52) U.S. Cl. ................. 435/5; 435/70.21; 435/339.1; 435/346; 424/147.1; 530/388.35; 530/413
(58) Field of Search ................ 435/5, 70.2, 70.21, 435/172.2, 235, 236, 239, 240.27, 339.1, 346.1; 424/86, 147.1; 530/413, 388.35

(56) References Cited

PUBLICATIONS

Harlow et al., Antibodies A Laboratory Manual, Cold Spring Harbor Laboratory, Cold Spring, 1988, pp. 148–152 and 567–569.*
Britt et al., J. Immunol. 130: 2363–2367, 1983.*
Sevier et al., Clin. Chem. 27: 1797–1806. 1981.*
Gangemi, J.D., 9–(2–Phosphonylmethoxyethyl)Adenine in the Treatment of Murine Acquired Immunodeficiency Disease and Opportunistic Herpes Simplex Virus Infections, Anti–Microbial Agents and Chemotherapy (1989) 33:1865–1868.
Research Agreement for Material provided by NIAID, NIH to Kay Townsend, Mar. 17, 1988 for Tissue culture supernatant of monoclonal antibody 83A25.
Research Agreement for Material provided by NIAID, NIH to Paul Hoffman, Baltimore, Maryland, Apr. 14, 1988 for 83A25.
Research Agreement for Material provided by NIAID, NIH to David Onions, Apr. 8, 1988 for Monoclonal antibodies against murine retrovirus envelope proteins. University of Glasgow.
Research Agreement for Material provided by NIAID, NIH to Marguerite Hays, Veterans Admin., May 25, 1988 for monoclonal antibodies to murine leukemia virus envelope proteins.
Research Agreement for Material provided by NIAID, NIH to David Gangemi, Columbia, S.C., Feb. 10, 1989 for HeLa CD4 positive clone 6C cells–hybridomas 83A25, 514, 516, 7 also 18–7.
Research Agreement for Material provided by NIAID, NIH to Robert Cozens, Basle, Switzerland, Feb. 20, 1989 for hybridomas 83A25, 514, 48, 516, 7, also anti–p30 18–7.
Material Transfer Agreement to Carol Funk, Tucson, Arizona, Sep. 11, 1989 for 83A25.
Material Transfer Agreement to Alan Rein, Frederick Maryland, Nov. 6, 1989 for MAbs as tissue culture supernatant—MAbs 83A25, 514, Hy7, 516 and 502.
Material Transfer Agreement to Dr. Randy Hock, Charlottesville, Virginia, Nov. 8, 1989 for MAb 83A25.
Material Transfer Agreement to Dr. Sidney Grossberg, Milwaukee, Wisconsin, Jan. 17, 1990, for Monoclonal antibodies reactive toward MuLV envelope proteins.
Material Transfer Agreement to Igor Roninson, Chicago, Illinois, Nov. 13, 1989, for Mouse monoclonal antibody 83A25.
Material Transfer Agreement to Piechaczyk Marc, France, Nov. 16, 1989, for Monoclonal antibody 83A25 as tissue culter supernatant.
Material Transfer Agreement to Didier Trono, Cambridge, Massachusetts, Dec. 15, 1989 for Monoclonal antibody 83A25 as tissue culture supernatant.
Material Transfer Agreement to Victor Garcia, Seattle, Washington, Jan. 25, 1990, for MAb 83A25 in the form of tissue culture supernatant.

* cited by examiner

*Primary Examiner*—Donna C. Wortman
(74) *Attorney, Agent, or Firm*—Townsend and Townsend and Crew, LLP

(57) ABSTRACT

A method for detecting broad spectrum of murine leukemia viruses belonging to any or all of the ecotropic, xenotropic, polytropic and amphotropic groups, has been described. The method utilizes a monoclonal antibody designated 83A25 which identifies almost all classes or groups of the murine leukemia virus with only a few exceptions.

7 Claims, 6 Drawing Sheets

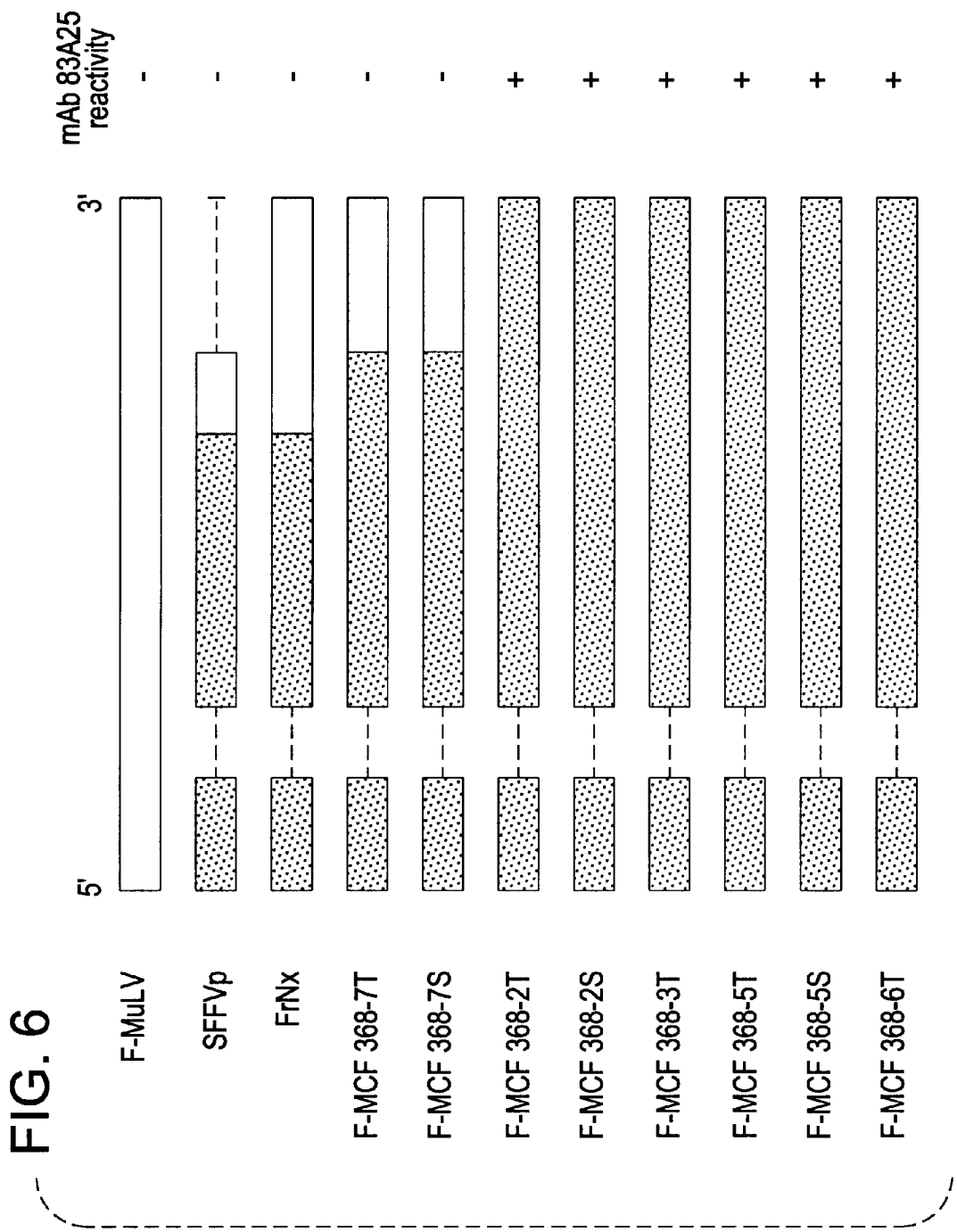

VERSATILE REAGENT FOR DETECTING MURINE LEUKEMIA VIRUSES

This is a Continuation Ser. No. 07/528,714, filed May 24, 1990, now abandoned.

The present invention is related generally to the preparation of diagnostic reagents. More particularly, the present invention is related to the preparation of an immunological reagent including a monoclonal antibody (MAb) reactive with an epitope found universally in all murine leukemia viruses (MuLVs) with only a few exceptions.

A variety of immunological reagents including MAbs directed at the proteins of MuLVs are known. These include MAbs specific for certain ecotropic, xenotropic and polytropic MuLVs from inbred mice and MAbs reactive with ecotropic viruses of feral mice. The antibodies have been employed in serological typing of different MuLVs, in histological localization of MuLV gene products in infected tissues; in flow cytometry to quantitate MuLV gene expression on the surface of cells; in radioimmune precipitation and immunoblotting of virally encoded proteins; in virus neutralization, and in quantitative assays of different types of MuLVs in complex mixtures of viruses.

However, MAbs differ greatly with respect to their applicability to the various procedures noted above. Those which efficiently detect cell surface antigen may not efficiently precipitate proteins or react in immunoblots. Some of the MAbs which react strongly with live cells, react poorly with fixed histological sections, and few of the MAbs exhibit a marked viral neutralizing activity even though many of them are reactive with viral envelope glycoproteins. Most of the available MAbs are reactive with only limited groups of viruses.

A versatile method for identifying the presence of virtually all classes, groups or strains of MuLVs has not heretofore been known or described.

SUMMARY OF THE INVENTION

It is, therefore, an object of the present invention to provide a versatile method for detecting MuLVs belonging to any or all of the ecotropic, xenotropic, polytropic as well as the amphotropic class of MuLVs.

It is a further object of the present invention to provide an immunological reagent of broad applicability for MuLVs including focal immunofluorescence assays on live or fixed monolayers, immunoblotting, immunoprecipitation, immunohistochemical, flow cytometric procedures and the like.

It is another object of the present invention to provide a method for effectively neutralizing MuLVs of virtually all classes.

It is an additional object of the present invention to provide a reliable method for screening cultures for the presence of MuLV.

Various other objects and advantages will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 6 represents the Ecotropic and polytropic regions of the envelope glycoproteins of recombinant derivatives of F-MuLV. Sequences encoding the envelope glycoproteins of F-MuLV. MAb 83A25-reactive and unreactive F-MuLV-derived polytropic MuLVs, and of the Lilly-Steeves strain of SFFV are depicted by bar diagrams. Open (white) regions of the diagrams correspond to sequences derived from the ecotropic F-MuLV parent. Solid (black) regions correspond to sequences derived from endogenous polytropic-like sequences. Areas of the bar diagrams which are interrupted by dashed lines correspond to sequences which are deleted from the polytropic and SFFV envelope genes when compared to the ecotropic F-MuLV sequences. The indicated deletions have been confirmed by nucleotide sequence analysis in the case of SFFV$_p$ (Wolff et al, 1983, *Proc. Natl. Acad. Sci. USA*, 80:4718–4722) and FrNx (Adachi et al, 1984, *J. Virology*, 50:813–821) and are assumed to be present in the remaining polytropic isolates. Additional small deletions which minimally affect the colinearity between F-MuLV and its derivatives are not indicated.

DETAILED DESCRIPTION OF THE INVENTION

Figure 1:
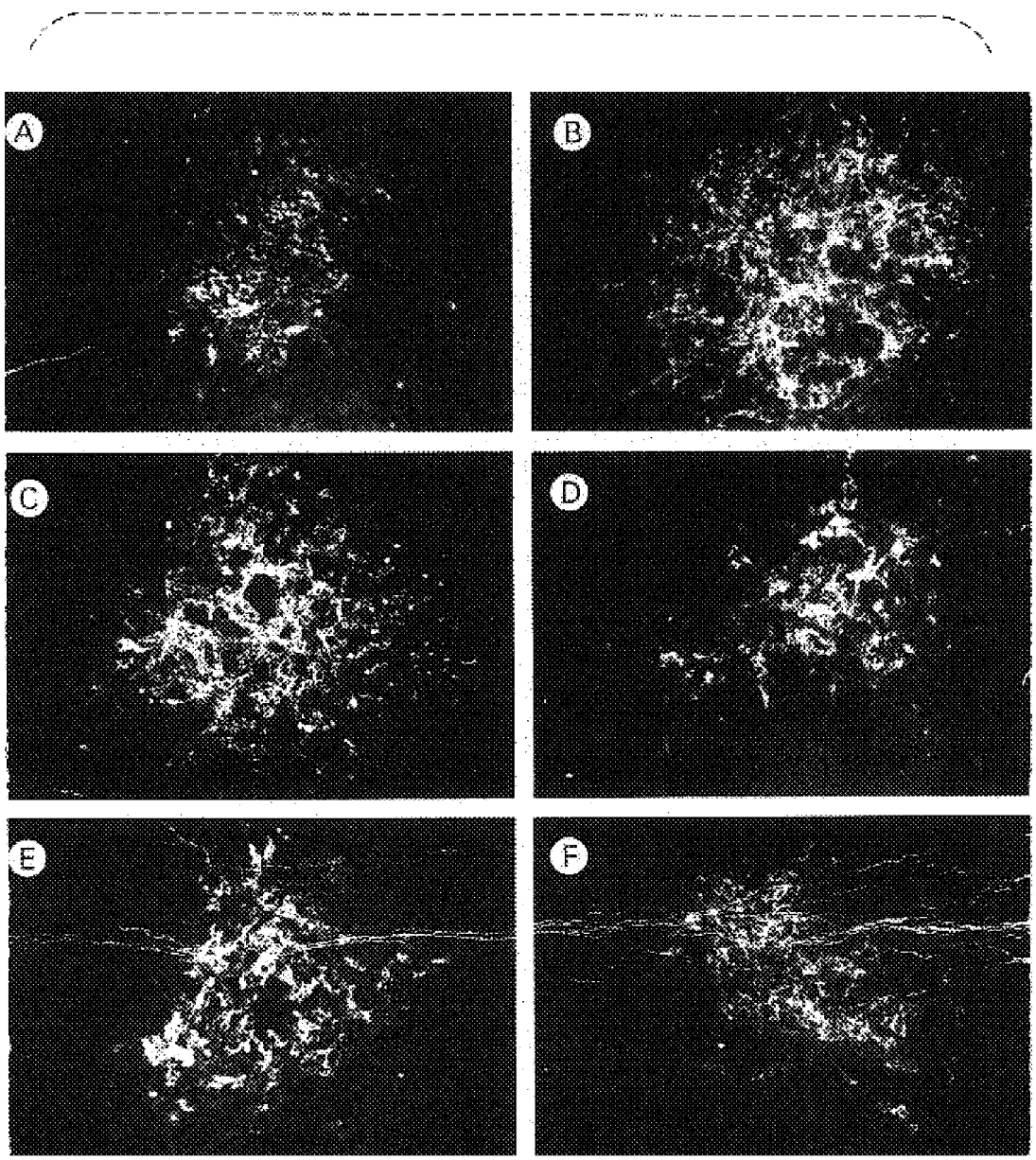
FIGS. 1(A),(B),(C),(D),(E),(F) demonstrates fluorescent detection of ecotropic, polytropic, xenotropic and amphotropic MuLV infections on live monolayers with MAb 83A25. Following infection of cell cultures by MuLVs the cells were allowed to grow to confluency and assayed for focal infections by the FIA using MAb 83A25. (A) Ecotropic MuLV AKR 2A on M. dunni cells; (B) polytropic MuLV M72P-S on M. dunni cells; (C) polytropic MuLV M73P-S on M. dunni cells; (D) polytropic MuLV M73P-S on Mv1Lu mink lung fibroblasts; (E) xenotropic MuLV Balb IU-1 on Mv1Lu mink lung fibroblasts; (F) amphotropic MuLV 1504A on Mv1Lu mink lung fibroblasts. Magnification 25× before enlargement.

The above and various other objects and advantages of the present invention are achieved by an immunological reagent comprising an MAb designated herein as 83A25.

A deposit of the hybridoma secreting the 83A25 MAb has been made at the ATCC, Rockville, Md., on Mar. 21st 1990 under accession number HB10392. The deposit, by Dr. Leonard H. Evans of Rocky Mountain Laboratories, 903 South Fourth Street, Hamilton, Mo. was tested and proven viable on Mar. 23, 1990 by ATCC, shall be viably maintained, replacing if it becomes non-viable during the life of the patent, for a period of 30 years from the date of the deposit, or for 5 years from the last date of request for a sample of the deposit, whichever is longer, and upon issuance of the patent made available to the public without restriction in accordance with the provisions of the law. The Commissioner of Patents and Trademarks, upon request, shall have access to the deposit.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

MATERIALS AND METHODS

Viruses and Cells

Friend MuLV 57 (F-MuLV) (Oliff et al, 1980, *J. Virol.*, 33:475–486), Moloney MuLV 1387 (M-MuLV) (Evans and Duesberg, 1982, *J. Virol.* 41:735–743), F-MCF-1 (Troxler et al, 1978, *J. Exp. Med.*, 148:639–653), and Friend virus complexes consisting of the Lilly-Steeves strain of the spleen focus-forming virus (SFFV$_p$) or an anemia strain of SFFV (SFFVa) and ecotropic F-MuLV 57 helper virus (Evans et al, 1980, *Quant. Biol.* 44:823–835) were originally obtained as chronically infected Fischer rat embryo (FRE) cells from E. M. Scolnick (Merck Sharp and Dohme Research Laboratories, West Point, Pa.). The ecotropic viruses AKR 2A (Cloyd et al, 1979, *J. Exp. Med.*, 149:702–712) and WN1802N (Cloyd et al, 1980, *J. Exp. Med.* 151:542–552); the polytropic viruses AKR L5 (Cloyd et al, supra), AKR 247 (Hartley et al, 1977, *Proc. Natl. Acad. Sci. USA*, 74:789–792), AKR L3 (Cloyd et al, supra), AKR 6AS (Chattopadhyay et al, 1981, *Virology*, 113:465–483), AKR 6AT (Chattopadhyay et al, supra), AKR 13 (Cloyd et al, supra), Akv-2-C34 (Cloyd et al, supra), Akv-1-C44-2 (Cloyd et al, supra) and HIX (Fischinger et al, 1975, *Proc. Natl. Acad. Sci. USA*, 72:5150–5155); the xenotropic viruses AKR 6 (Cloyd et al, supra), NIH AT124 (Todaro et al, 1973, *Proc. Natl. Acad. Sci. USA*, 70:859–862), C58L1 Xeno (Chattopadhyay et al, supra), Cas E No. 1 (Cloyd et al, supra), Balb I-U1 (Hartley and Rowe, 1976, *J. Virol.*, 19:19–25, NFS-Th1 (Chattopadhyay et al, supra), NZB-8882 (Rein and Schultz, 1984, *Virology* 136:144–152) and NZB Cl. 35 (Levy et al, 1975, *J. Virol.* 16:844–853); and the amphotropic viruses 1504A and 4070A (Hartley and Rowe, supra) were obtained from M. W. Cloyd (Univ. of Texas Medical Branch, Galveston, Tex.). The wild mouse ecotropic viruses CasBr-E (Hartley and Rowe, supra) and 1504 E (Hartley and Rowe, supra) were provided by J. Hartley (Natl. Inst. Allergy and Infectious Diseases, Bethesda, Md.). The ecotropic F-MuLV strains F-MuLV-N-87 (Chesebro et al, 1983, *Virology*, 127:134–148), 25-57-NB (Chesebro et al, supra), 29-39-NB (Chesebro et al, supra), F-MuLV 67 (Chesebro et al, supra), I-5 (FB 7) (Mathieu-Mahud et al, 1982, *Virology*, 119:59–67; Sitbon et al, 1986, *Cell*, 47:851–859), I-5 (FB 29) (Mathieu-Mahud et al, supra: Sitbon et al, supra), 643/22N [Ostertag and Pragnell, 1978, *Proc. Natl. Acad. Sci. USA*, 75:3278–3282; Pragnell et al, 1978, *Nature* (London), 272:456–458], 643/22F (Ostertag and Pragnell, supra; Pragnell et al, supra), and R-MuLV (Chesebro et al, 1981, *Virology*, 112:31–144; Rauscher, 1962, *J. Natl. Cancer Inst.*, 29:515–543) were obtained from B. Chesebro (Rocky Mountain Laboratories, Hamilton, Mont.). The polytropic isolate MCF-FrNx (Adachi et al, 1984, *J. Virology*, 50:813–821) was obtained from A. Ishimoto (Kyoto University, Sakyo-ku, Kyoto, Japan). The origin of the F-MCF 1E has previously been described (Chesebro et al, 1984, *J. Virol.* 51:63–70). The polytropic viruses 368-2T, 368-2S, 368-3T, 368-5T, 368-5S, 368-6T, 368-7T, and 368-7S were isolated from NFS/N mice after inoculation of ecotropic F-MuLV 57 (Evans and Cloyd, 1984, *J. Virol.*, 49:772–781). Polytropic viruses 383-1T, 383-1S, 383-2T, 383-2S, 383-4T, 383-4S, 383-5T and 383-5S were isolated from NFS mice after inoculation of ecotropic M-MuLV 1387 (Evans and Cloyd, 1985, *Proc. Natl. Acad. Sci. USA*, 82:459–463). Polytropic viruses M60P-T, M62P-S, M72P-S, M73P-S, M75P-T, M75P-S, M79P-T and M81P-S were isolated from AKR/J mice (Evans, 1986, *Virology*, 153:122–136; Evans and Malik, 1987, *J. Virol.*, 61:1882–1892).

All viruses except M-MuLV and the Friend virus complexes were propagated on M. dunni cells (Lander and Chattopadhyay, 1984, *J. Virol.*, 52:695–698). M-MuLV was propagated on Sc-1 cells (Hartley and Rowe, 1975, *Virology*, 65:128–134) while the Friend virus complexes were maintained as the originally infected FRE cells. Purified virus preparations were accomplished by sedimentation followed by isopycnic density gradient centrifugation as described by Evans et al, 1979, *J. Virol.*, 31:133–146. Other cell lines employed in these studies were Mv1Lu mink lung fibroblasts (ATCC CCL64) and the NS-1 nonsecretor clone, P3-NS-1-1-Ag4/1 of MOPC21 myeloma cells (Kohler and Milstein, 1976, *Eur. J. Immunology*, 6:511–519). Infected and uninfected M. dunni, SC-1 and FRE cells were grown in MEM (Gibco) supplemented with 5% fetal calf serum (FCS). Mink cells were grown in Dulbecco's modified MEM supplemented with 10% FCS. NS-1 and hybridoma cell lines were maintained in RPMI supplemented with 10% FCS.

Antibodies

83A25 was one of several hybridoma cell lines obtained after immunization of a Fischer Rat with an extract of a purified virion preparation of F-MCF 368-2T (Evans and Cloyd, supra). The rat was inoculated in the foot pads with 1 mg of virion protein derived from a Triton ×100-disrupted, ether extracted virion preparation in complete Freund's adjuvant, as previously described (Evans et al, 1977, *J. Virol.*, 24:865–874). Three weeks later the rat received a subcutaneous booster inoculation with 1 mg of the antigen preparation in incomplete Freund's adjuvant and the spleen cells from the rat were used in fusions with NS-1 cells 3 days following the booster inoculation. Techniques for the fusion of cells, detection of antibody producing hybridomas and subsequent cloning of the hybridomas were done as described by Chesebro et al, supra. The isotype of the mAb released by 83A25 (mAb 83A25) was determined to be of the IgG 2a class using a rat monoclonal typing kit (ICN ImmunoBiologicals) according to the manufacturers instructions. In all experiments the source of mAb 83A25 was tissue culture media from saturated cultures of hybridoma cells cleared by centrifugation at 15,000× g for 10 minutes. Unless otherwise indicated the media was used undiluted.

Other MuLV-reactive antibodies utilized in this study included mAb 48 (reactive with the envelope proteins of F-MuLV and R-MuLV) (Chesebro et al, supra), mAb R146 (reactive with p15 from several MuLVs) and mAb R186 (reactive with p30 from several MuLVs), both derived from Mendell-Osbourn rats immunized with SFFV-infected NRK cells, and goat anti-gp70 serum provided by Dr. J. Cole, Biological Carcinogenesis Branch, NCI, Bethesda, Md.

Determination of Reactivity of mAb 83A25 with MuLV Strains

The reactivity of mAb 83A25 with various strains of MuLVs was determined by cell surface fluorescence of infected cells as described by Chesebro et al, supra. Briefly, cells infected with individual virus strains were trypsinized, rinsed in PBBS (Chesebro and Wehrly, 1976, *J. Exp. Med.*, 143:73–84) containing 2% FCS (rinsing buffer) and incubated with the antibody for 30 minutes at 37° C. The cells were rinsed twice in rinsing buffer and incubated with FITC-conjugated goat anti-mouse Ig (Sigma, cat. # F 9006) diluted 1:200 in PBBS for 30 minutes at 37° C. The cells were then rinsed three times in rinsing buffer and examined for membrane fluorescence under a Leitz orthoplan incident light fluorescent microscope equipped with a 100 watt light source.

Cytoplasmic Fluorescence Assays

In some cases cells were examined for cytoplasmic fluorescence. In these instances the cells were grown on 13 mm coverslips to confluency. The coverslips were rinsed in 25 mM sodium phosphate-0.15M sodium chloride, pH 7.2 (PBS) and then immersed in acetone prechilled to −20° C. for 20 minutes and allowed to dry at ambient temperature. The coverslips were then rehydrated with PBS and incubated for 60 minutes at ambient temperature with undiluted hybridoma tissue culture supernatants. Following washing, a FITC conjugated goat anti-rat IgG antiserum (Southern Biotechnology Associates Inc.) diluted 1:100 was added and incubated for 60 minutes as above. The coverslips were washed two times for 10 minutes, counterstained with 0.2% Evans blue in water for 10 minutes, washed in PBS as above, mounted under PBS:glycerol (70:30) and examined for fluorescence as described above.

Virus Neutralization and Focal Immunofluorescence Assay for MuLVs

For neutralization, virus stocks were adjusted to approximately $2\times10^2$/ml and then diluted 1:1 with serial dilutions of mAb 83A25, mAb 48 or with fresh media and incubated for 30 minutes at 37° C. Virus titers of the mAb-treated and control samples were determined as described below.

Quantitative assays of MuLVs were performed using a focal inimunofluorescence assay (FIA) (Sitbon et al, 1985, *Virology* 141:110–118). Tissue culture plates were inoculated with a quantity of cells such that confluency of the monolayer would be reached after 6 days ($5\times10^4$ cells/60 mm dish for M. dunni cells, $10^5$ cells/60 mm dish for SC-1 and mink lung fibroblasts). After one day the cells were infected by the addition of 0.5 mls of an MuLV sample diluted 1:10 with tissue culture media containing 8 ug/ml polybrene. The infecting media was changed with fresh tissue culture media (without polybrene) the next day and thereafter at two day intervals until the cells were confluent. The monolayers were rinsed with rinsing buffer and incubated with 100–200 ul of mAb 83A25 for 30 minutes at 37° C. The cells were rinsed twice to remove unbound mAb, then incubated with 100–200 ul of goat anti-mouse Ig (1:200 in PBBS) for 30 minutes at 37° C. The monolayers were then rinsed three times and the dishes examined using the Leitz orthoplan fluorescent microscope equipped with a 100 watt light source, 8× ocular eyepieces and a 10×/0.4 objective.

SDS-PAGE, Electrophoretic Transfer, and Immunoblotting

SDS-PAGE and immunoblotting were essentially done as described by Morrison et al, 1989, *J. Exp. Med.*, 169:663–675. SDS-PAGE was performed on virion lysates with a 12.5% gel. After electrophoresis, polypeptides were electrophoretically transferred to nitrocellulose paper (NCP), and the NCP was incubated in PBS containing 3% bovine serum albumin and 0.05% Tween 20 (blocking buffer) for 30 minutes at room temperature (about 22°–24° C.). The NCP was then incubated with 50 mls of goat anti-gp70 serum (diluted 1/500 in blocking buffer) or mAb 83A25 (1/5 dilution of culture supernatant in blocking buffer) overnight at room temperature, then washed three times with PBS containing 0.05% Tween 20. For detection of polypeptides immunoreactive with the goat anti-gp70 serum, the NCP was incubated with 50 ml of $^{125}$I-protein A (50,000 cpm/ml) in blocking buffer for 2 h at room temperature, washed 3 times with PBS containing 0.05% Tween 20, washed once with water, air dried and subjected to autoradiography with Kodak X-Omat AR film and a Lightning-Plus intensifying screen overnight at −70° C. For detection of polypeptides immunoreactive with mAb 83A25, the NCP was incubated for 2 h at room temperature with 50ml of affinity purified rabbit anti-rat IgG (#61-620-1 ICN Biomedicals, Inc.) diluted 1/500 in blocking buffer, washed 3 times with PBS containing 0.05% Tween 20, reacted with $^{125}$I-protein A, and processed for autoradiography as described above.

Radiolabeling of Viruses and Cells

Virus preparations to be radioiodinated were first dialyzed against PBS and intact virions corresponding to approximately 50 ug of protein for each preparation were iodinated by the chloramine T method as described by Greenwood et al, 1963, *Biochem. J.*, 89:114–123. Free iodine was removed by extensive dialysis. 50 ng of iodinated virions were prepared for immunoprecipitation by solubilizing in 5 mls of RIPA buffer (0.1% SDS, 1.0% NP40 and 1.0% DOC in Tris-buffered saline, pH 7.4) for 20 minutes at 4° C.

For $^{35}$S-methionine labeling of infected cells, confluent cultures were washed three times in PBS and then incubated at 37° C. for 1 h in methionine-free Dulbecco's modified Eagle media. The cultures were then incubated for 6 h in methionine-free media containing 100 uCi/ml of $^{35}$S-methionine. Following the incubation period, the monolayer was washed twice with PBS, subjected to one freeze thaw cycle and then solubilized with RIPA buffer. Incorporation of the radiolabel was determined by assaying trichloroacetic acid precipitable cpm in each sample.

Immunoprecipitation $^{35}$S-methionine cellular extracts or $^{125}$-labeled virus in RIPA buffer were incubated with 1/8 volume of formalin fixed Staph A bacteria (Calbiochem, San Diego, Calif.) at 4° C. overnight. The solution was precleared by ultracentrifugation at 75,000 rpm for 60 minutes and aliquots were incubated overnight at 4° C. with either 5 μl of goat anti gp70 serum or 0.5 mls of mAb. Antigen-antibody complexes were collected by the sequential addition of goat anti-rat IgG and Staph A bacteria. The precipitates were repeatedly washed in RIPA buffer until minimal radioactivity was detected in the buffer. Antigen-antibody complexes were then disrupted by boiling for 3 minutes in disruption buffer (0.2% SDS, 5% 2-mercaptoethanol in Tris-buffered saline, pH 7.4). Precipitated proteins were analyzed by SDS-PAGE in 8% gels and processed for fluorography as described by Britt et al, 1981, *J. Exp. Med.*, 154:868–882.

Immunohistochemistry

Skeletal muscle from the hind limb of infected and uninfected mice were frozen in liquid nitrogen and 6 micron sections made on a cryostat (American optical HistoStat). All subsequent procedures were carried out at room temperature. Sections were fixed 2 minutes in 1.5% formaldehyde, washed twice for 10 minutes each in PBS and incubated for 30 minutes with undiluted mAb 83A25 tissue culture supernatant. After two subsequent 10 minute washes in PBS a specific FITC conjugated goat anti-rat IgG antiserum (Southern Biotechnology Associates Inc., Birmingham, Ala.) diluted $\frac{1}{100}$ was added and incubation carried out for 30 minutes at room temperature. After two washes as above the sections were examined using a Leitz Orthoplan microscope with epifluorescence.

RESULTS

Reactivity of mAb 83A25 with MuLVs

Cell lines infected with MuLVs exhibit virally coded cell surface antigens, thus the reaction of an antibody with a particular MuLV can be conveniently determined by the binding or lack of binding of the antibody to infected cells. The binding of mAb 83A25 to MuLV-infected cells was determined for a large array of MuLVs of different classes derived from a variety of sources (Tables 1 and 2). MAbs other than 83A25 were reactive only with specific types of MuLVs, usually limited to certain isolates of a particular MuLV group (i.e., ecotropic, polytropic or xenotropic MuLVs). In contrast mAb 83A25 exhibited a remarkably broad specificity with MuLVs, reacting with almost all MuLVs tested regardless of the class or source of the virus. This included most polytropic and all xenotropic MuLVs from inbred mouse strains that were tested, as well as all ecotropic MuLVs tested except F- and R-MuLVs. Polytropic viruses which did not react with the antibody were limited to certain recombinant derivatives of F-MuLVs. The mAb also exhibited strong reactivity to viruses from feral mice including the wild mouse ecotropic MuLVs CasBr-E and 1504 E. the Cas E No. 1 xenotropic MuLV and the amphotropic MuLVs 1504A and 4070A.

The anemia and polycythemia strains of SFFV were tested for membrane fluorescence and found to be negative (Table 2). Since SFFV-infected cells have been reported to exhibit low levels of cell surface envelope protein (Ruta and Kabat, 1980, *J. Virol.*, 35:844–853), SFFV-infected cells were also examined for reactivity with mAb 83A25 by cytoplasmic fluorescence. Under conditions in which cells infected with amphotropic virus (1504A) were easily identified by cytoplasmic fluorescence, assays of SFFV-infected cells were negative (not shown) suggesting that the gene products of this virus do not contain the proper epitope.

Utility of mAb 83A25 in MuLV Assays

The broad reactivity of mAb 83A25 facilitated the assays of all of the reactive MuLVs using the FIA. FIG. 1 illustrates the detection of focal infections of ecotropic, amphotropic, polytropic and xenotropic MuLVs on different cell lines. Focal infections were apparent for all reactive viruses and could be enumerated on each of the permissive cell lines. In each case the assay was clearly dose responsive (not shown). The assays can be performed on live monolayers, as was done in the assays shown in FIG. 1, or on fixed cells. In the former instance viruses can be biologically cloned by subculturing foci of infected cells directly from the assay.

Protein Immunoblotting and Radioimmune Precipitation Using mAb 83A25

Figure 2:
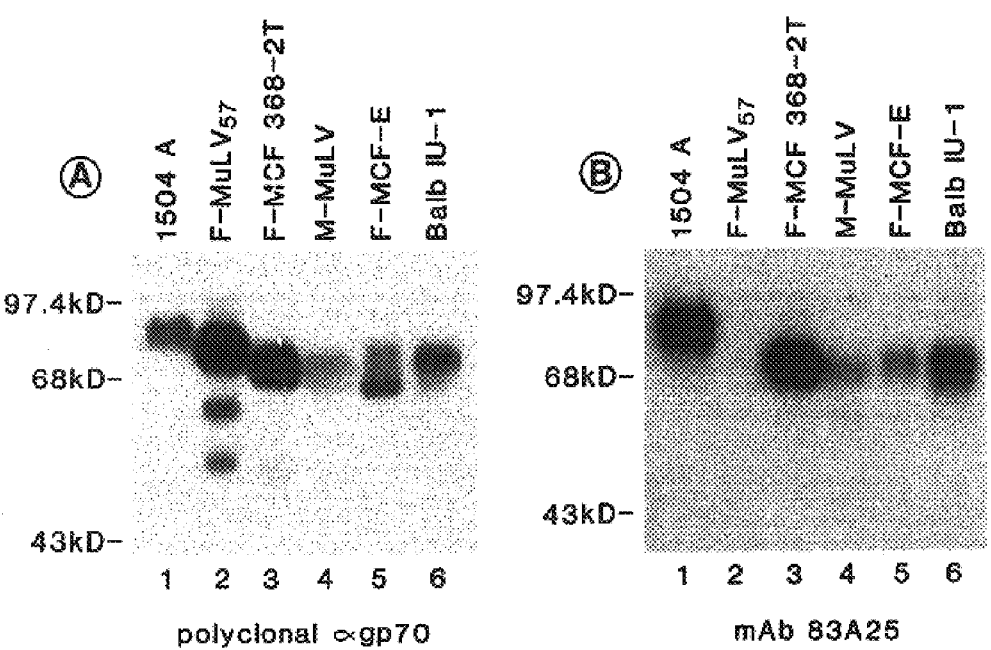
FIGS. 2(A),(B) shows protein blot immunoassay of virion proteins with MAb 83A25. Virion preparations were dissociated, electrophoresed in 12.5% SDS-polyacrylamide gels and electrophoretically transferred to nitrocellulose paper. Parallel blots were reacted with MAb 83A25 2(B) or with goat anti-gp70 serum 1(A) and bound antibody detected as described in Materials and Methods.
Figure 3:
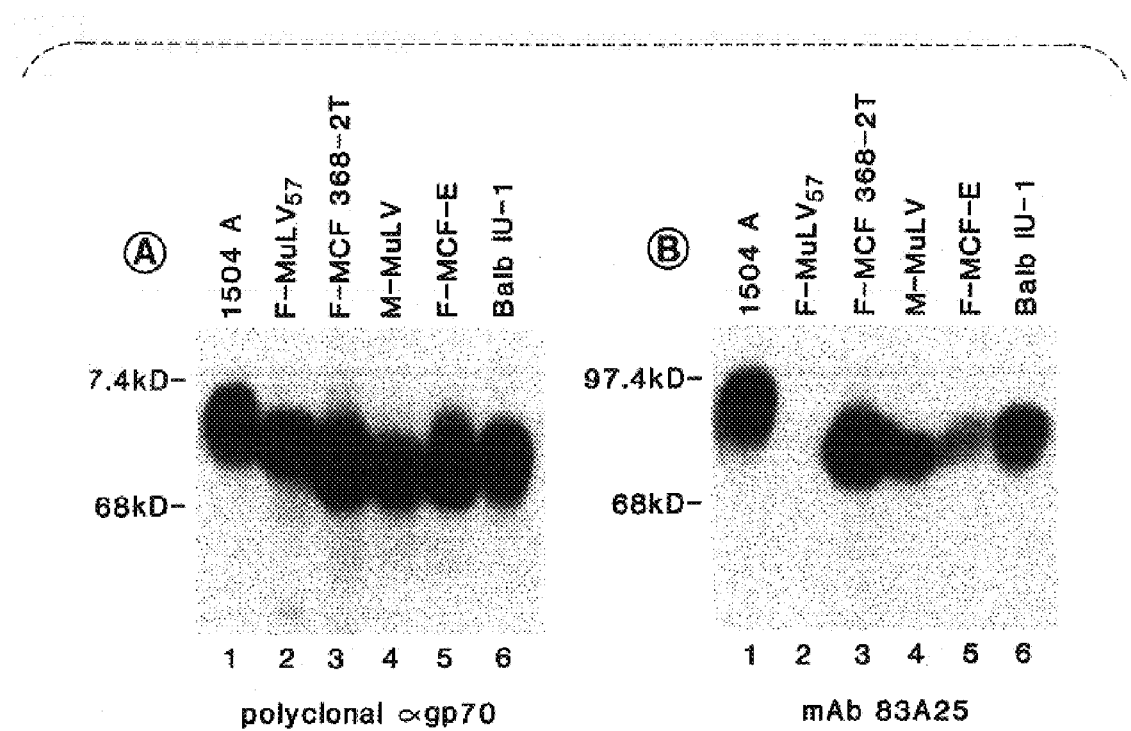
FIGS. 3(A),(B) shows the results of SDS-PAGE analysis of virion proteins immunoprecipitated by MAb 83A25. $^{125}$I-labeled virions were immunoprecipitated with MAb 83A25 3(B) in conjunction with goat anti-rat IgG, or with goat anti-gp70 serum 3(A). The immunoprecipitates were analyzed in 8% SDS-polyacrylamide gels.

The mAb was tested for its utility in protein immunoblotting and in radioimmune precipitation procedures using purified virus preparations from representatives of each of the virus classes (FIGS. 2 and 3). Immunoblots and radioimmune precipitations were done in parallel using either mAb 83A25 or a broadly reactive anti-gp70 antiserum. Quite similar proteins were detected by the mAb and the antiserum in both procedures and indicated that the antibody was specific for the MuLV envelope glycoproteins. Of the viruses tested, all reacted except F-MuLV 57, which is in agreement with the membrane fluorescence data present above. For some viruses (e.g. M-MuLV and F-MCF-E) the proteins detected by the polyclonal antiserum appeared more heterogeneous than those detected by mAb 83A25. The additional proteins detected by the antiserum may represent envelope protein breakdown products which have lost the epitope reactive with MAb 83A25. With both the antiserum and the mAb there was considerable variation in the intensity of the glycoprotein bands. The virion preparations employed in the immunoblots and radioimmune precipitations were normalized with respect to total protein, however the level of the envelope glycoproteins can very widely in different virus preparations. Thus, it is not clear if the different intensities of the bands in FIGS. 2 and 3 are due to different levels of the glycoprotein in the various preparations or, alternatively, to variations in the efficiency of detection of the glycoproteins. Considering that mAb 83A25 detected denatured proteins in the immunoblot (FIG. 2), it is likely that it is reactive with an epitope corresponding to a primary structure of the protein rather than a complex epitope conferred by protein conformation. It is noteworthy that mAb 83A25 is the first reported mAb reactive with the envelope glycoproteins of amphotropic MuLVs.

To further test the reactivity of SFFV-encoded proteins with mAb 83A25, extracts of metabolically radiolabeled infected cells were subjected to immunoprecipitation procedures using mAb 83A25 or polyclonal antiserum to the envelope glycoprotein. The antiserum readily precipitated envelope glycoprotein-related products from both SFFV and amphotropic MuLV 1504A-infected cells whereas mAb 83A25 precipitated proteins from 2504A-infected cells, but failed to precipitate proteins from SFFV-infected cells (data not shown). These results further indicated that SFFV does not encode an epitope reactive with mAb 83A25.

Detection of MuLV Expression in Histological Section Using mAb 83A25

Figure 4:
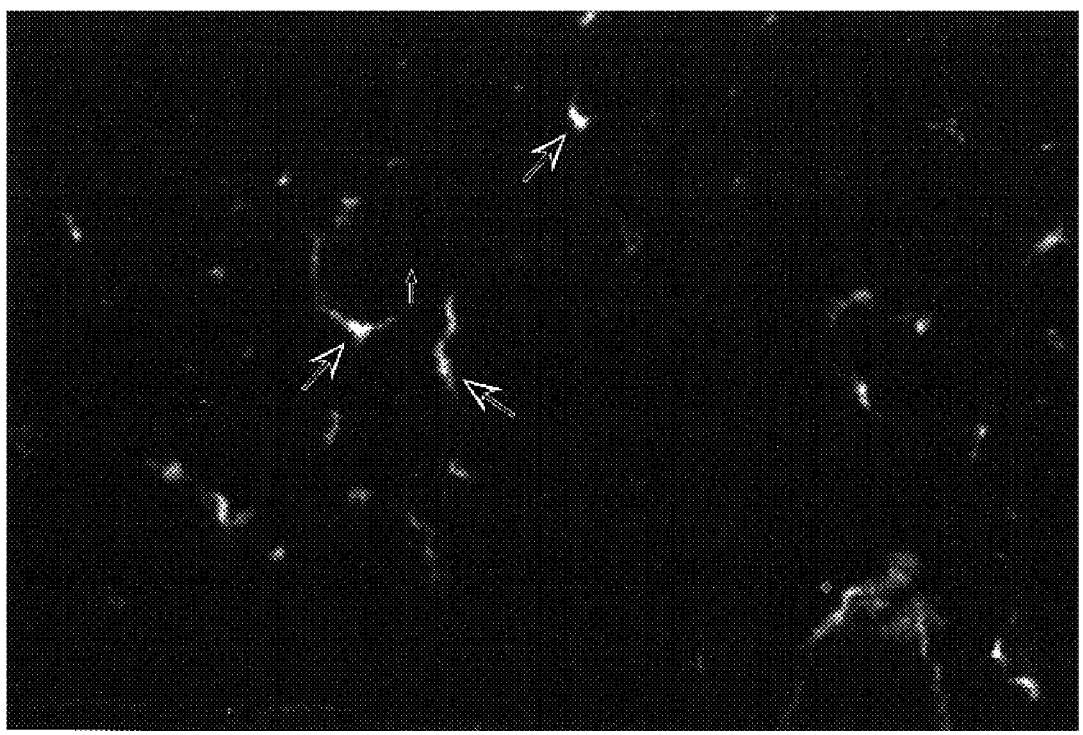
FIG. 4 shows a frozen section of the flexor muscles of the posterior femoral region of an IRW mouse 5 weeks after neonatal inoculation with CasBr-E. This mouse had clinical manifestations of neurologic disease (tremor, hind limb paralysis and muscle atrophy). The section was stained with MAb 83A25 and FITC-conjugated goat anti-rat IgG. The photomicrograph shows muscle cells in cross-section (small arrows), the cell borders being highlighted by viral antigen present in the interstitium between myocytes (large arrows). The myocytes themselves are negative for viral antigen. Magnification 64× before enlargement.

As noted earlier, a mAb of heterologous origin may facilitate studies of MuLV expression in histological sections without necessitating the direct fluorescent conjugation of the mAb. FIG. 4 demonstrates the detection of MuLV envelope expression in a cross-section of skeletal muscle from a mouse with paralytic disease resulting from inoculation with a biologically clones wild mouse ecotropic virus, CasBr-E. In this application, the section was incubated with mAb 83A25 and then detected with a FITC-conjugated polyclonal antiserum preparation specifically reactive with rat IgG. Controls consisted of skeletal muscle from uninfected mice as well as staining with the FITC conjugate alone. In both cases the background staining was almost absent. Viral envelope protein here is localized between and around muscle cells, a pattern consistent with the location of viral particles in skeletal muscle described by Gardner et al, 1973, *J. Natl. Cancer Inst.*, 51:1243–1249.

Figure 5:
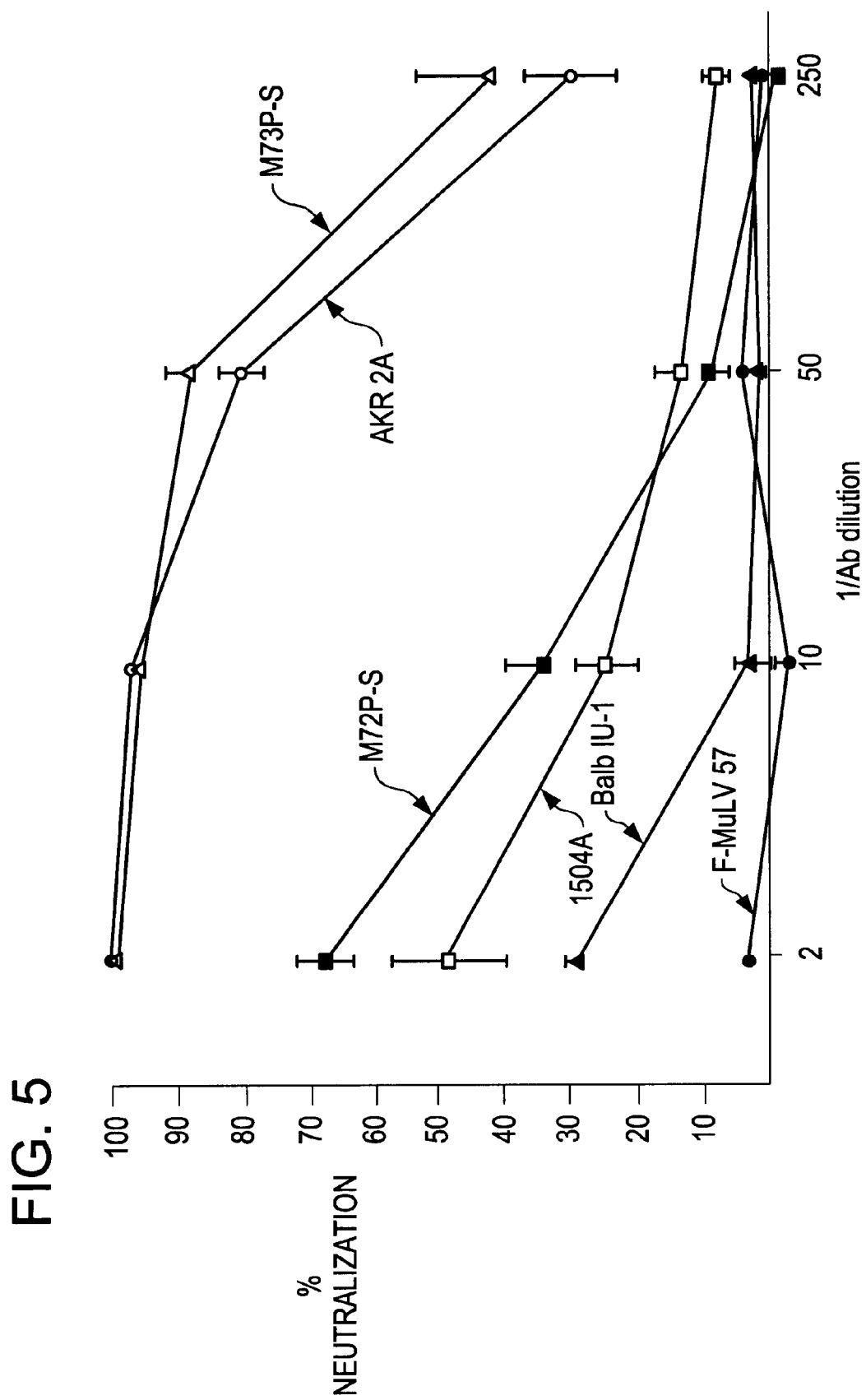
FIG. 5 demonstrates the neutralization of MuLV infectivity by MAb 83A25. Stocks of ecotropic (AKR 2A), Class I polytropic (M73P-S), Class II polytropic (M72P-S), xenotropic (Balb IU-1) and amphotropic (1504A) MuLVs were incubated with dilutions of hybridoma 83A25 tissue culture medium for 30 minutes. The treated MuLV stocks were subsequently assayed for infectivity on M. dunni (AKR 2A, M73P-S, M72P-S and 1504A) or Mv1Lu mink lung fibroblasts (Balb IU-1) using the FIA.

Virus Neutralization by mAb 83A25 mAb83A25 was tested for its ability to neutralize MuLV infectivity using the FIA (FIG. 5). Most mAbs tested in this laboratory have exhibited neutralizing activity of MuLVs only with the addition of guinea pig complement to the incubation of antibody with virus (Chesebro et al, supra). In contrast mAb 83A25 exhibited effective neutralization of MuLVs in the absence of added complement. The neutralization titers varied greatly with different reactive MuLVs, ranging from 50% neutralization titers of approximately 1:100 with the ecotropic virus AKR 2A and the polytropic MuLV M73P-S to titers of less than 1with the xenotropic virus Balb IC-1 using undiluted tissue culture supernatant from the hybridoma culture. In agreement with the immunofluorescent, immunoprecipitation and immunoblotting results above, F-MuLV infectivity was unaffected by the mAb, indicating its lack of reactivity. The efficiency of neutralization did not strictly correlate with virus interference groups, considering that the neutralization titer for the polytropic MuLV M73P-S was substantially higher than for the polytropic MuLV M72P-S. These polytropic MuLVs correspond to Class I and Class II polytopic viruses, respectively, both of which are subject to complete Interference by other polytropic MuLVs (Evans, supra: Evans and Malik, supra). In control experiments designed to test for non-specific inhibition, a mAb (mAb 48) unreactive with M73P-S or AKR 2A failed to affect the infectivity of these viruses.

In summary, a unique rat MAb 83A25 of the IgG2a isotype has been made that is reactive with the envelope glycoproteins of almost all MuLVs, including amphotropic MuLVs for which no mAbs reactive with envelope proteins have previously been described. the finding that mAb 83A25 reacts with nearly all MuLVs indicates the presence of a highly conserved epitope in the envelope glycoproteins of MuLVs. Yet the presence of this epitope is not required for efficient viral replication as evidenced by the lack of reactivity of the mAb with F-MuLV or R-MuLV, both of which are fully replication-competent viruses. The lack of reactivity of mAb 83A25 with F-MuLV was observed with all stains of F-MuLV tested and likely reflects the common origin of these strains from a single original isolate (Friend, 1957, *J. Exp. Med.*, 105:307–318). However R-MuLV, which is also unreactive, has an independent origin (Rauscher, supra). F-MuLV and R-MuLV have a unique pathogenicity among MuLVs in that they induce erythroleukemia in mice with a relatively short latency. It is possible that the lack of reactivity with mAb 83A25 reflects the presence of an alternative structure that influences the pathogenicity of the viruses. Although the viral LTRs have been shown to be a major determinant of the pathogenic spectrum of oncogenic MuLVs in terms of tissue specificity, it is clear that other regions of the genome also exert an influence.

The lack of reactivity of mAb 83A25 with F-MuLV, R-MuLV and certain polytropic MuLVs indicated the probable location of the reactive epitope on the glycoproteins. As noted earlier, the unreactive polytropic MuLVs were limited to those derived by recombination with F-MuLVs. Comparisons of the genomic structures of these derivatives revealed that each of them have retained the F-MuLV gene sequences encoding the carboxy terminus of the envelope glycoprotein. Conversely, all mAb 83A25-reactive polytropic derivatives of F-MuLV have acquired these sequences from endogenous polytropic-like sequences (Evans and Cloyd, supra). Furthermore, the replication-defective SFFVs, which are also recombinant derivatives of F-MuLVs, exhibit env-gene deletions which include the carboxy terminus of the envelope glycoprotein. A schematic representation of the genomic structures of reactive and non-reactive F-MuLV recombinant derivatives are presented in FIG. 6. It is quite likely from these comparisons that the epitope reactive with mAb 83A25 is encoded by sequences within the 3' one-third of the envelope glycoprotein coding region. Comparisons of published amino acid sequences of MuLVs in this region to the amino acid sequence of F-MuLV did not reveal an obvious candidate sequence for the epitope. Thus, further studies will be necessary to precisely define the immunoreactive domain.

Unconcentrated tissue culture media from hybridoma 83A25 exhibited virus neutralizing activity with representatives of ecotropic, polytropic, xenotropic and amphotropic MuLVs. Neutralization of different MuLV interference groups, which utilize different receptors on permissive cells, suggests that mAb 83A25 does not directly bind to receptor binding domains of the MuLVs. Moreover, strong determinants of in vitro host range are encoded within the 5' one-half of the envelope glycoprotein gene. If these determinants indeed correspond to receptor binding regions, it would appear that the epitope reactive with mAb 83A25 lies outside of the receptor binding domain, suggesting a stearic effect of antibody binding on infectivity. The efficiency of neutralization varied considerably among different isolates but did not correlate closely with virus interference groups. Indeed, the neutralization of the oncogenic polytropic MuLV, M73P-S, was approximately 50-fold higher than for the non-oncogenic polytropic isolate, M72P-S. Both of these viruses were derived from AKR/J mice and have 5' env-gene sequences that are indistinguishable by $T_2$-oligonucleotide fingerprinting (Evans and Malik. supra). However, the viruses differ with respect to the origins of the epitope reactive with mAb 83A25. M73P-S has derived the carboxy half of the glycoprotein from the ecotropic MuLV parent whereas the allelic region of M72P-S is derived from endogenous polytropic-like retroviral sequences. Among the possible explanations for the differences in neutralization between these two isolates are differences in their reactive epitopes resulting in different binding affinities for the antibody, or different tertiary structures of the envelope glycoproteins resulting in different stearic effects of antibody binding. An explanation for the neutralization differences may be facilitated when a more precise definition of the reactive epitope is available.

The broad reactivity of mAb 83A25 facilitates the assay of a wide range of MuLVs and provides an extremely useful screening reagent for infectious virus production or viral envelope expression. We routinely use the mAb to quantify titers of MuLV stocks and to detect MuLV production in tissues of mice by infectious center assays or MuLV expression in histological sections. In addition the mAb is useful for routine screening of cell lines for virus infection or release of infectious virions. As an example of the latter application we have detected the infection of human cells by viruses released from an amphotropic MuLV packaging cell line, even though the infection was not detected in viral polymerase assays. The antibody is effective in virtually all common immunological procedures including immunofluorescence of live or fixed cells and of fixed tissues in histological sections, immunoblotting or immunoprecipitation and in virus neutralization. The mAb has also been successfully employed in flow cytometry procedures. Clearly, the mAb is of substantial utility in murine retrovirology.

A reagent kit comprises a container containing immunoreactive amount of 83A25 monoclonal antibodies and instructional material to perform appropriate assays or tests. A composition of material in accordance with the present invention comprises an immunoreactive or neutralizing amount of the mAb 83A25 and a pharmaceutically acceptable carrier. A method for detecting the presence of MuLV comprises reacting a sample suspected of MuLV infection with the mAb 83A25, the occurrence of antigen-antibody reaction being indicative of the presence of MuLV in the tested sample.

In accordance with the present invention, it now becomes possible to purify leukemia virus by such means as affinity chromatography and the like. Typically, the antibody 83A25 is attached to a matrix such as Sepharose and the like. Then a solution containing the envelope glycoprotein is adsorbed to the matrix-antibody complex under binding conditions and the matrix-antibody-protein complex washed to remove the impurities. The envelope protein is then eluted from the matrix under non-binding conditions, e.g., high salt solution, and the purified virus or viral protein recovered.

It is understood that the examples and embodiments described herein are for illustrative purposes only and that various modifications or changes in light thereof will be suggested to persons skilled in the art and are to be included within the spirit and purview of this application and scope of the appended claims.

TABLE 1

Reactivity of mAb 83A25 with ecotropic, xenotropic and amphotropic MuLVs.

| Virus | Membrane Fluorescence |
|---|---|
| Ecotropic | |
| AKR 2A | + |
| WN1802N | + |
| CasBr-E | + |
| 1504E | + |
| M-MuLV | + |
| P-MuLV[a] | − |
| R-MuLV | − |
| Xenotropic | |
| AKR 6 | + |
| NIH AT124 | + |
| C58L1 xeno | + |
| Cas E No. 1 | + |
| Balb I-U1 | + |
| NFS-Th1 | + |
| NZB-8882 | + |
| NZB Cl. 35 | + |
| Amphotropic | |
| 1504A | + |
| 4070A | + |

[a]Nine strains of F-MuLV (see Materials and Methods for strain identities) were tested and found to be uniformly unreactive with mAb 83A25.

TABLE 2

Reactivity of mAb 83A25 with recombinant MuLVs.

| Recombinant Virus | Membrane Fluorescence |
|---|---|
| Akv-derived | |
| AKR L5 | + |
| AKR 247 | + |
| AKR L3 | + |
| AKR 6AS | + |
| AKR 6AT | + |
| AKR 13 | + |
| Akv-2-C34 | + |
| Akv-1-C44-2 | + |
| M60P-T | + |
| M62P-S | + |
| M72P-S | + |
| M73P-S | + |
| M75P-T | + |
| M75P-S | + |
| M79P-T | + |
| M81P-S | + |
| M-MuLV-derived | |
| HIX | + |
| 383-1T | + |
| 383-1S | + |
| 383-2T | + |
| 383-2S | + |
| 383-4T | + |
| 383-4S | + |
| 383-5T | + |
| 383-5S | + |
| F-MuLV-derived | |
| 368-2T | + |
| 368-2S | + |
| 368-3T | + |
| 368-5T | + |
| 368-5S | + |
| 368-6T | + |
| 368-7T | − |
| 368-7S | − |
| MCF-FrNx | − |
| F-MCF 1 | − |
| F-MCF 1E | + |
| SFFVp | − |
| SFFVa | − |

What is claimed is:

1. A hybridoma secreting monoclonal antibody 83A25 having the identifying characteristics of ATCC deposit no. HB 10392.

2. A method of detecting murine leukemia virus (MuLV) in a sample or a culture, comprising:

a) contacting said sample or culture with a monoclonal antibody against a common epitope that specifically binds monoclonal antibody 83A25, said epitope being present on the envelope glycoproteins of ecotropic, xenotropic, polytropic, and amphotropic murine leukemia virus, under conditions such that an immunocomplex can form between said monoclonal antibody and said envelope glycoprotein epitope; and b) detecting the presence of an immunocomplex consisting essentially of said monoclonal antibody and said envelope glycoprotein.

3. The method according to claim 2, wherein said murine leukemia virus is selected from the group consisting of ecotropic, xenotropic, polytropic, and amphotropic MuLV.

4. A method for neutralizing murine leukemia virus in vitro, comprising:

reacting murine leukemia virus with a sufficient amount of a monoclonal antibody against a common epitope that specifically binds monoclonal antibody 83A25, said epitope being present on the envelope glycoproteins of ecotropic, xenotropic, polytropic, and amphotropic murine leukemia virus, to form a neutralizing immunocomplex between said monoclonal antibody and said envelope glycoprotein epitope.

5. A method for purifying leukemia virus or viral protein comprising attaching antibody 83A25 to a matrix and adsorbing the leukemia virus or viral protein to said attached antibody, thereafter washing the impurities and then eluting the adsorbed virus or the viral protein from said matrix and recovering the purified virus or viral protein.

6. A monoclonal antibody against a common epitope on the envelope glycoprotein of ecotropic, xenotropic, polytropic, and amphotropic murine leukemia virus that specifically binds monoclonal antibody 83A25.

7. A reagent kit comprising a container having an immunoreactive amount of monoclonal antibody 83A25 and instructional materials to perform appropriate assays or tests.

* * * * *